United States Patent [19]

Taylor, Jr. et al.

[11] Patent Number: 5,162,322
[45] Date of Patent: Nov. 10, 1992

[54] METHOD OF TREATING ANXIETY WITH 5-[(4-ARYL OR HETEROARYL-1-PIPERAZINYL]ALKYL)-2-OXAZOLIDINONES

[75] Inventors: Chandler R. Taylor, Jr., Mechanicsville; L. Meredith Moses, Glen Allen, both of Va.; Brian F. Kilpatrick, Chesterfield, Mo.

[73] Assignee: A. H. Robbins Company, Incorporated, Richmond, Va.

[21] Appl. No.: 665,093

[22] Filed: Mar. 6, 1991

[51] Int. Cl.$^5$ .................. A61K 31/50; A61K 31/495
[52] U.S. Cl. ................................................ 514/252
[58] Field of Search ........................................ 514/252

[56] References Cited

U.S. PATENT DOCUMENTS

| | | | |
|---|---|---|---|
| 3,419,559 | 12/1968 | Lunsford et al. | 544/364 |
| 3,455,941 | 7/1969 | Lunsford et al. | 260/295 |
| 3,457,267 | 7/1969 | Lunsford et al. | 260/291 |
| 3,513,236 | 5/1970 | Lunsford et al. | 424/26 |
| 4,886,794 | 12/1989 | Walsh | 514/24 |

OTHER PUBLICATIONS

The Merck Manual-10th Ed, pp. 1717-1720 (1961).

Primary Examiner—Leonard Schenkman
Attorney, Agent, or Firm—Robert F. Boswell, Jr.

[57] ABSTRACT

This invention discloses the antianxiety properties of compounds of the formula:

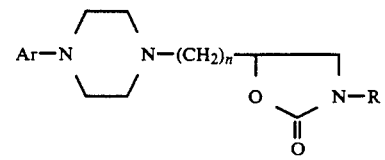

wherein n is 3 or 4, R is $C_1$–$C_4$ alkyl or phenyl, and Ar is

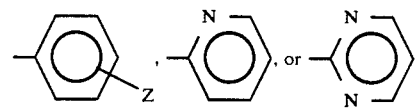

where Z is selected from H, $C_1$–$C_4$ alkoxy, $C_2$–$C_4$ alkenyloxy or hydroxy.

18 Claims, No Drawings

METHOD OF TREATING ANXIETY WITH 5-[(4-ARYL OR HETEROARYL-1-PIPERAZINYL]ALKYL)-2-OXAZOLIDINONES

BACKGROUND OF THE INVENTION

1. Field of Invention

This invention relates to 5-[(4-aryl or heteroaryl-1-piperazinyl)alkyl]-2-oxazolidinones that have anxiolytic properties and a pharmaceutical composition for treating anxiety in warm blooded animals, including humans.

2. Information Disclosure Statement

U.S. Pat. No. 3,419,559, 3,455,941; 3,457,267 and 3,513,236 disclose oxazolidinones including those of Formula A:

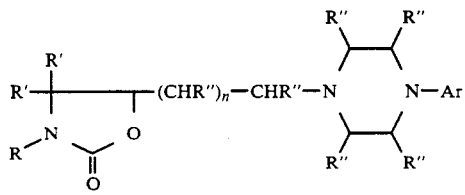

wherein R is H, loweralkyl, cycloalkyl or benzyl;
R' is H or loweralkyl independently;
R" is H or loweralkyl independently;
n is 1 or 2; and
Ar is phenyl or substituted phenyl.

Compounds of Formula A are disclosed as having tranquilizer and analgetic properties. Intermediates useful in preparing compounds of Formula A are disclosed in U.S. Pat. No. 3,423,418.

U.S. Pat. No. 4,886,794 discloses antiallergy 2-oxazolidinones of Formula B which encompasses.

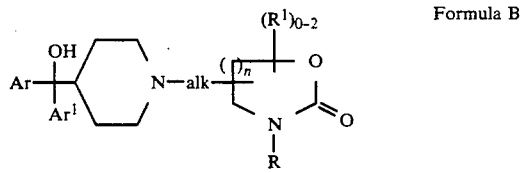

Formula B the 5-substituted oxazolidinones. A copending U.S. application, Ser. No. 07/633,030 filed Dec. 24, 1990 discloses antiallergy properties of certain 5-[(4-aryl-1-piperazinyl)alkyl]-2-oxazolidinones.

SUMMARY OF THE INVENTION

The compounds useful in the method and pharmaceutical composition of this invention are represented by Formula I below:

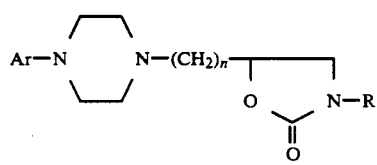

Formula I

Under Formula I, n is 3 or 4, R is $C_1$–$C_4$ alkyl or phenyl, Ar is

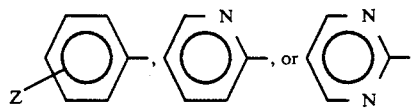

where Z is H, $C_1$–$C_4$ alkoxy, $C_2$–$C_4$ alkenyloxy or hydroxy. Also encompassed by Formula I are the stereoisomers and pharmaceutically acceptable salts.

More specifically, $C_1$–$C_4$ alkyl includes methyl, ethyl, propyl, isopropyl, butyl, sec-butyl, isobutyl, and tertiary butyl; $C_1$–$C_4$ alkoxy includes methoxy, ethoxy, propoxy, 2-propyloxy, butoxy, 2-butyloxy, isobutyloxy, and t-butyloxy; $C_2$–$C_4$ alkenyloxy includes vinyloxy, 2-propenyloxy, 2-(or 3)-butenyloxy and the like. The term pharmaceutically acceptable salts includes hydrates, solvates, and acid addition slats formed from inorganic or organic acids such as hydrochloric, hydrobromic, sulfuric, phosphoric, maleic, succinic, fumaric, citric, hexamic, tartaric and ethanesulfonic acids and the like.

Anxiolytic properties were determined using an in vitro assay in which competive binding with the 5-$HT_{1A}$ specific agonist, [$^3$H]8-hydroxy-2-(di-n-propylamino)tetralin(8-OH-DPAT) to 5$HT_{1A}$ receptors in the dog hippocampus membrane preparation is measured [Hall et al, J. Neurochem. 44, 1685–1696 (1985)]. Anxiolytic agents that bind selectively to the 5-$HT_{1A}$ receptor are of the class of anxiolytics represented by buspirone (Buspar ®), gepirone, and ipsapirone. Several compounds were also tested in mice is the exploratory light/dark method as described by Young and Johnson, Soc. Neurosci. Abs. 1988, 14, 207 in which the exploratory behavior of a mouse is a two-compartment light-dark activity box is monitored electrically and behavioral variables such as time spent in the lit versus dark compartments, rearings in either of the two compartments, number of transitions between the two compartments and other exploratory behavioral variables are recorded. Significant increases in one or more of the variables associated with the exploratory behavior of the animal in the lit area versus the dark area correspond to active non-sedating anxiolytic compounds.

DETAILED DESCRIPTION OF THE INVENTION

The compounds useful in this invention are prepared following procedures previously disclosed in U.S. Pat. Nos. 3,419,559; 3,455,941; 3,457,267; 3,513,236 and 4,886,794 and in J. Pharm. Sci. 58(3), 362–364 and are hereby incorporated by reference. The invention compounds are prepared according to Scheme A.

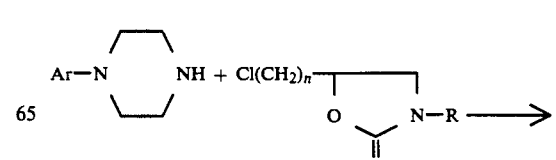

A.

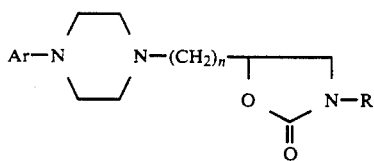

This reaction is typically performed using a polar solvent such as ethanol, butanol, or dimethyl formamide at or near the boiling point of the solvent with an acid acceptor such as sodium carbonate, potassium carbonate or sodium bicarbonate present. Potassium iodide may be used to catalyze the reaction. The product is isolated and purified by conventional methods.

Scheme B indicates the reaction used to obtain the alkenyloxy substituted invention compounds.

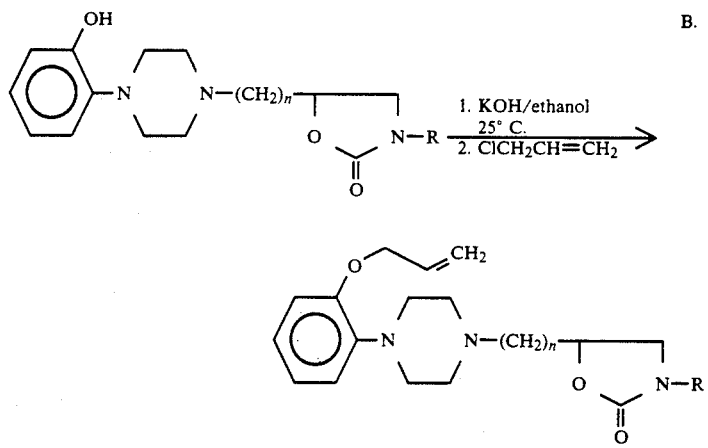

B.

The 5-haloalkyl-2-oxazolidinones are obtained from the appropriate N-substituted aminomethyltetrahydrofuran or the corresponding tetrahydropyran according to Scheme C.

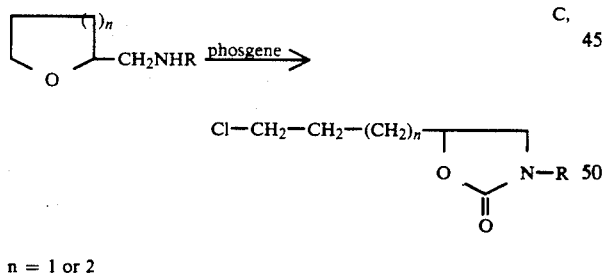

C.

n = 1 or 2

This ring-opening/ring closure reaction is carried out in an aprotic solvent at or below ambient temperature. The precursor substituted aminomethyltetrahydrofuran or pyran are prepared from the commercially available 2-(chloromethyl)tetrahydrofuran or pyran and the desired amine as shown in Scheme D.

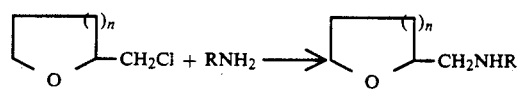

D.

n = 1 or 2

Excess amine serves as the solvent in the procedure of Scheme D.

The above procedures are broadly described and actual reaction conditions will depend on the reaction temperatures, solvents, purity of reactants and the like. The following Preparations and Examples are illustrative of the above reaction schemes and should not be construed as limiting to this disclosure in any way. Reactants for which no preparative procedure is given are either commercially available or readily prepared using published procedures. It is expected that one skilled in the art would be able to carry out this invention without undue experimentation.

PREPARATION 1

Tetrahydro-N-(1-methylethyl)-2H-pyran-2-methanamine ethanedioate (1:1).

A solution of 2-(bromomethyl)tetrahydro-2H-pyran (100 g, 0.558 mol) and isopropylamine (66.0 g, 1.12 mol) was refluxed under nitrogen overnight, and the solvent was removed under reduced pressure. A 3N hydrochloric acid solution was added to acidify the residue, and the solution was washed twice with ether and made basic with a 50% sodium hydroxide solution. The product was extracted twice into ether, and the combined extracts were washed twice with a saturated sodium chloride solution, dried (sodium sulfate), filtered, and evaporated under reduced pressure to an oil (54.8 g, 62% yield). A portion of the oil (13.7 g, 0.0873 mol) was dissolved in warm 2-propanol and a solution of oxalic acid (7.86 g, 0.0873 mol) in warm 2-propanol was added. A solid precipitated, which was collected by filtration and dried under high vacuum at 60° C. to give 17.24 g, mp 172°–175° C.

Analysis: Calculated for $C_{11}H_{12}NO_8$: C, 53.43; H, 8.56; N, 5.66; Found: C, 53.54; H, 8,94; N, 5.60.

PREPARATION 2

Tetrahydro-N-phenyl-2H-pyran-2-methanamine.

A mixture of 2-(bromomethyl)tetrahydro-2H-pyran (100 g, 0.558 mol) and aniline (155.96 g, 1.67 mol) was heated at 100° C. under nitrogen overnight and cooled to room temperature. A 3N hydrochloric acid solution (400 mL) was added and the aqueous layer was washed three times with isopropyl ether. The aqueous layer was made basic with 50% sodium hydroxide solution, and the product was extracted three times into isopropyl ether. The combined organic extracts were washed once with water and evaporated under reduced pressure. The resulting oil was poured into water (1400 mL) and stirred. The water was decanted and water (1500 mL) was again added. The aqueous layer was again decanted and the oil was triturated again in water (1500 mL) to give a solid, which was recrystallized from methanol/water and dried under high vacuum to give 78.5 g of product containing one mole of water (67% yield). A 2.0 g portion was recrystallized from methanol/water and dried under high vacuum to give 0.71 g, mp 55°–58° C.

Analysis: Calculated for $C_{12}H_{17}NO$: C, 75.35; H, 8,96; N, 7.32; Found: C, 75.33; H, 9.15; N, 7.25.

PREPARATION 3

Tetrahydro-N-phenyl-2-furanmethanamine ethanediodate (1:1).

A mixture of tetrahydrofurfuryl chloride (100 g, 0.829 mol), aniline (2.09 g, 2.25 mol) and potassium iodide (1.0 g) was heated at 130° C. under nitrogen for 36 hours and cooled to room temperature. A 3N hydrochloric acid solution (400 mL) was added and the solution was washed several times with isopropyl ether and made basic with a 50% sodium hydroxide solution. The product was extracted three times into isopropyl ether, washed twice with water and once with a saturated sodium chloride solution, dried (sodium sulfate), filtered and evaporated to a liquid that was added to water (3L) and extracted into three portions of isopropyl ether. The combined extracts were washed twice with water and once with a saturated sodium chloride solution, dried (magnesium sulfate), treated with charcoal, filtered and evaporated under reduced pressure to a liquid (91.4 g). A 6.0 g portion was dissolved in isopropanol and a solution of oxalic acid (3.1 g) in isopropanol was added. The resulting solid was collected by filtration and rinsed with isopropyl ether to give 6.3 g of solid. A 1.5 g portion was recrystallized from isopropanol/isopropyl ether/light pet ether to give a solid that was removed by filtration. A second crop of crystals was obtained from the filtrate, dried under high vacuum at 60° C. to give 0.31 g, mp 149°–156° C.

Analysis: Calculated for $C_{13}H_{17}NO_5$: C, 58.42; H, 6.41; N, 5.24; Found: C, 57.99; H, 6.41; N, 5.37.

PREPARATION 4

5-(4-Chlorobutyl)-3-(1-methylethyl)-2-oxazolidinone.

A solution of phosgene (287 mL of a 20% solution, 273 g, 0.55 mol) in toluene and additional toluene (100 mL) was cooled to −10° C. by an ice/methanol bath and a solution of tetrahydro-N-(1-methylethyl)-2H-pyran-2-methanamine (41.13 g, 0.262 mol) and triethylamine (27.9 g, 0.276 mol) in toluene (300 mL) was added dropwise, keeping the temperature below 5° C. The mixture was warmed to room temperature and refluxed under nitrogen for 30 min. Zinc chloride (0.65 g) was added and refluxing was continued for 15 min. An additional portion of zinc chloride (0.32 g) was added, and the mixture was refluxed for 24 hr and allowed to stand at room temperature for several days. Water (750 mL) was added, and the layers were separated. The organic layer was washed twice again with water and once with a saturated sodium chloride solution, dried (magnesium sulfate), treated with charcoal, filtered, and evaporated to an oil. The oil was distilled under reduced pressure, and the fraction distilling from 148°–165° C./0.3 mm was collected to give 46.7 g (81% yield).

Analysis: Calculated for $C_{10}H_{18}NO_2Cl$: C, 54.67; H, 8.26; N, 6.38; Found: C, 53.37; H, 8.37; N, 6.15.

PREPARATION 5

5-(3-Chloropropyl)-3-phenyl-2-oxazolidinone.

To a solution of phosgene in toluene (342 g of a 20% solution, 0.693 mol) was added additional toluene (150 mL) and the solution was cooled to −10° C. in an ice/methanol bath. Dropwise, keeping the temperature below 5° C., a solution of 2-phenylaminomethyltetrahydrofuran (58.4 g, 0.330 mol) and triethylamine (35.1 g, 0.348 mol) in toluene (400 mL) was added. The mixture was warmed to room temperature and then refluxed for 30 minutes. Zinc chloride (0.82 g) was added and refluxing was continued for 15 minutes. An additional portion of zinc chloride (0.41 g) was added and the mixture was refluxed under nitrogen for 24 hours. The mixture was washed twice with water, once with a saturated sodium chloride solution, dried (sodium sulfate), filtered, and evaporated under reduced pressure to an oil, which crystallized upon standing (70.7 g, 89% yield). Recrystallization from isopropanol/isopropyl ether gave 47.0 g of solid, from which a 1.5 g portion was again recrystallized from isopropanol/isopropyl ether and dried under high vacuum to give 1.18 g, mp 76°–79° C.

Analysis: Calculated for $C_{12}H_{14}NO_2Cl$: C, 60.13; H, 5.89; N, 5.84; Found: C, 60.11; H, 5.97; N, 5.81.

PREPARATION 6

5-(4-Chlorobutyl)-3-phenyl-2-oxazolidinone.

To a 20% solution of phosgene in toluene (273 g of solution, 0.55 mol) was added toluene (100 mL) and the solution was stirred in an ice/methanol bath. A solution of 2-phenylaminomethyltetrahydropyran (50.0 g, 0.262 mol) and triethylamine (27.9 g, 0.276 mol) in toluene (300 mL) was added dropwise, keeping the temperature below 5° C. The mixture was warmed to room temperature and then refluxed for 30 minutes. Zinc chloride (0.65 g) was added and the mixture was refluxed for 15 minutes. An additional portion of zinc chloride (0.32 g) was added and the mixture was refluxed for 10 minutes and stirred at room temperature for 3 days. The mixture was again refluxed for 24 hours, cooled to room temperature, washed twice with water, and twice with a saturated sodium chloride solution, dried (magnesium sulfate), treated with charcoal, filtered, and evaporated under reduced pressure to give 57.8 g (87% yield) of solid, which was recrystallized from isopropanol/isopropyl ether to give 38.0 g of product. A 1.5 g portion was gain recrystallized from isopropanol/isopropyl ether and dried under high vacuum to give 0.92 g, mp 65°–69° C.

Analysis: Calculated for $C_{13}H_{16}NO_2Cl$: C, 61.54; H, 6.36; N, 5.52; Found: C, 61.50; H, 6.44; N, 5.50.

EXAMPLE 1

3-Methyl-5-[4-(4-phenyl-1-piperazinyl)butyl]-2-oxazolidinone.

A mixture of 5-(4-chlorobutyl)-3-methyl-2-oxazolidinone (10.0 g, 0.0524 mol), 1-phenylpiperazine hydrochloride (0.0524 mol, 10.39 g), potassium carbonate (28.94 g, 0.209 mol) and potassium iodide (1.0 g) was refluxed in 1-butanol (150 mL) for 24 hr and then stirred at room temperature for two days. The mixture was reheated to boiling and filtered hot. Methanolic hydrogen chloride was added to acidify the filtrate and addition of isopropyl ether caused a solid to precipitate. The solid was collected by filtration and dissolved in water. Potassium carbonate was added to make the solution basic and the product was extracted into two portions of ethyl acetate. The combined ethyl acetate layers were washed twice with water, three times with a saturated sodium bicarbonate solution and once with a saturated sodium chloride solution. The solution was dried (sodium sulfate), filtered, and evaporated under reduced pressure to an oil. Addition of isopropyl ether gave a solid which was recrystallized from isopropyl ether/methanol. The solid was collected by filtration, rinsed with light pet ether and dried under high vacuum to give 7.51 g (45% yield), mp 85°–88° C.

Analysis: Calculated for $C_{18}H_{27}N_3O_2$: C, 68.11; H, 8.57; N, 13.24; Found: C, 68.10; H, 8.68; N, 13.28.

EXAMPLE 2

3-Methyl-5-[4-[4-(2-pyridinyl)-1-piperazinyl]butyl]-2-oxazolidinone.

Following the procedure of Example 1, the title compound is prepared from a mixture of 5-(4-chlorobutyl)-3-methyl-2-oxazolidinone (5.0 g, 0.0262 mol), 1-(2-pyridinyl)piperazine (4.56 g, 0.0279 mol) and potassium carbonate (8.5 g, 0.0614 mol) in 1-butanol (50 ml) to obtain 3.4 g (41%) of solid. Recrystallization from ethyl acetate/petroleum ether followed by drying in vacuo gave 1.46 g of the title compound, mp 69°–72° C.

Analysis: Calculated for $C_{17}H_{26}N_4O_2$: C, 64.12; H, 8.23; N, 17.60; Found: C, 64.01; H, 8.29; N, 17.58.

EXAMPLE 3

5-[4-[4-(2-Methoxyphenyl)-1-piperazinyl]butyl]-3-methyl-2-oxazolidinone dihydrochloride.

Following the procedures of Example 1, the title compound is prepared. Thus, a mixture of 5-(4-chlorobutyl)-3-methyl-2-oxazolidinone (5.0 g, 0.0262 mol), 1-(2-methoxyphenyl)piperazine (5.4 g. 0.0279 mol), potassium carbonate (8.5 g, 0.0614 mol), and potassium iodide (0.75 g) in 1-butanol (50 ml) gave 6.8 g of oil which was dissolved in hot methanol and acidified with methanolic hydrogen chloride. Addition of isopropyl ether and isopropanol to the cloud point and cooling gave a solid which was collected by filtration, rinsed with isopropyl ether and light pet ether and dried under high vacuum to give 4.22 g (38% yield), mp 209°–216° C.

Analysis: Calculated for $C_{19}H_{29}N_3O_3.2HCl$: C, 54.28; H, 7.43; N, 10.00; Found: C, 54.16; H, 7.72; N, 9.98.

EXAMPLE 4

3-Methyl-5-[4-[4-(2-pyrimidinyl)-1-piperazinyl]butyl]-2-oxazolidinone.

Following the procedure of Example 1, mixture of 5-(4-chlorobutyl)-3-methyl-2-oxazolidinone (5.0 g, 0.0262 mol), 1-(2-pyrimidinyl)piperazine dihydrochloride (6.62 g, 0.0279 mol), potassium carbonate (19.3 g, 0.140 mol) and potassium iodide (0.75 g) in 1-butanol (75 ml) gave an oil (3.0 g) which crystallized upon standing. Recrystallization from ethyl acetate/light pet ether followed by drying under high vacuum gave 1.33 g (16% yield), mp 74°–76° C.

Analysis: Calculated for $C_{16}H_{25}N_5O_2$: C, 60.17; H, 7.89; N, 21.92; Found: C, 60.02; H, 8.02; N, 21.96.

EXAMPLE 5

5-[3-[4-(2-Methoxyphenyl)-1-piperazinyl]propyl]-3-methyl-2-oxazolidinone hydrochloride hydrate (2:2:3).

A mixture of 5-(3-chloropropyl)-3-methyl-2-oxazolidinone (5.0 g, 0.0282 mol), 1-(2-methoxyphenyl)piperazine (5.43 g, 0.0282 mol), potassium carbonate (11.71 g, 0.0847 mol), and potassium iodide (0.5 g) in 1-butanol (75 mL) was refluxed for 24 hours under nitrogen and filtered hot. A 3N hydrochloride acid solution was added to acidify the filtrate, and the aqueous solution was washed twice with isopropyl ether. The aqueous solution was made basic with potassium carbonate, and the product was extracted into two portions of ethyl acetate. The combined ethyl acetate layers were washed three times with water and once with a saturated sodium chloride solution, dried (sodium sulfate), filtered, and evaporated under reduced pressure to an oil (7.1 g, 76% yield). The oil was dissolved in hot isopropanol, acidified with ethereal hydrogen chloride, and allowed to cool. The resulting solid was collected by filtration, rinsed with diethyl ether, and dried under high vacuum at 60° to give 6.92 g, mp 199°–202° C.

Analysis: Calc. for $C_{18}H_{27}N_3O_3.HCl.1.5H_2O$: C, 54.47; H, 7.87; N, 10.59; Found: C, 54.23; H, 7.53; N, 10.50.

EXAMPLE 6

3-Methyl-5-[3-[4-(2-pyridinyl)-1-piperazinyl]propyl]-2-oxazolidinone hydrochloride hydrate (2:4:1).

Following the procedure of Example 5, a mixture of 5-(3-chloropropyl)-3-methyl-2-oxazolidinone (5.0 g, 0.0282 mol), 1-(2-pyridinyl)piperazine (4.61 g, 0.0282 mol), potassium carbonate (11.71 g, 0.0847 mol), and potassium iodide (0.5 g) in 1-butanol (75 mL) gave an oil (4.2 g, 49% yield). The oil was dissolved in hot isopropanol and acidified with ethereal hydrogen chloride. Methanol was added to make a solution. Upon cooling, a solid precipitated which was collected by filtration, rinsed with diethyl ether, and dried under high vacuum at 60° C. to give 3.66 g, mp 214°–218° C.

Analysis: Calc. for $C_{16}H_{24}N_4O_2.2HCl.0.5H_2O$: C, 49.74; H, 7.04; N, 14.50; Found: C, 49.73; H, 7.22; N, 14.51.

EXAMPLE 7

3-Methyl-5-[3-[4-(2-pyrimidinyl)-1-piperazinyl]propyl]-2-oxazolidinone.

Following the procedure of Examples 5, 5-(3-chloropropyl)-3-methyl-2-oxazolidinone (5.0 g, 0.0282 mol), 1-(2-pyrimidinyl)piperazine dihydrochloride (6.70 g, 0.0282 mol), potassium carbonate (23.4 g, 0.1695 mol), and potassium iodide (0.5 g) in 1-butanol (100 mL) gave an oil (3.5 g, 41% yield) which was dissolved in a hot mixture of isopropyl ether and isopropanol, filtered hot, and brought to the cloud point by the addition of light pet ether. Upon cooling, a solid precipitated which was collected by filtration, rinsed with light pet ether, and dried under high vacuum to give 1.38 g, mp 79°–89° C.

Analysis: Calculated for $C_{15}H_{23}N_5O_2$: C, 59.00; H, 7.59; N, 22.93; Found: C, 58.96; H, 7.75; N, 22.91.

EXAMPLE 8

5-[3-[4-(2-Ethoxyphenyl)-1-piperazinyl]propyl]-3-methyl-2-oxazolidinone.

Following the procedure of Example 5, a mixture of 5-(3-chloropropyl)-3-methyl-2-oxazolidinone (5.0 g, 0.0282 mol), 1-(2-ethoxyphenyl)piperazine monohydrochloride (6.86 g, 0.0282 mol), potassium carbonate (15.62 g, 0.113 mol), and potassium iodide (1.0 g) in n-butanol (100 mL) gave an oil (4.5 g, 46% yield). The oil was triturated in warm isopropyl ether and the resulting suspension was stirred at room temperature. The solid was collected by filtration, rinsed with light pet ether and dried under high vacuum to give 2.58 g, mp 79°–81° C.

Analysis: Calculated for $C_{19}H_{29}N_3O_3$: C, 65.68; H, 8.41; N, 12.09; Found: C, 65.80; H, 8.55; N, 12.07.

EXAMPLE 9

5-[4-[4-(2-Ethoxyphenyl)-1-piperazinyl]butyl]-3-methyl-2-oxazolidinone dihydrochloride.

Following the procedure of Example 5, a mixture of 5-(2-chlorobutyl)-3-methyl-2-oxazolidinone (5.2 g, 0.0272 mol), 1-(2-ethoxyphenyl)piperazine monohydrochloride (6.61 g, 0.0272 mol), potassium carbonate (15.05 g, 0.109 mol), and potassium iodide (1.0 g) in n-butanol (100 mL) gave an oil which was dissolved in a mixture of ethyl acetate/isopropyl ether/light pet ether (removing the impurities by filtration) and acidified with ethereal hydrogen chloride. The mixture was evaporated under reduced pressure and recrystallized once from isopropanol/methanol/isopropyl ether and then from isopropanol/isopropyl ether and dried under high vacuum at 60° C. to give 1.18 g (10% yield), mp 207°–212° C.

Analysis: Calculated for $C_{20}H_{31}N_3O_3.2HCl$: C, 55.30; H, 7.66; N, 9.67; Found: C, 55.14; H, 7.79; N, 9.61.

EXAMPLE 10

5-[3-[4-(2-hydroxyphenyl)-1-piperazinyl]propyl]-3-methyl-2-oxazolidinone.

Following the procedure of Example 5, a mixture of 1-(2-hydroxyphenyl)piperazine dihydrobromide (9.6 g, 0.0282 mol), 5-(3-chloropropyl)-3-methyl-2-oxazolidinone (5.0 g, 0.0282 mol), sodium bicarbonate (9.5 g, 0.113 mol), and potassium iodide in 1-butanol (100 ml) gave an oil. The oil was triturated several times with light pet ether (decanting each time) and dissolved in ethyl acetate/isopropyl ether. Cooling the solution gave a solid which was collected by filtration and dried under high vacuum to give 1.80 g (20% yield), mp 112°–116° C.

Analysis: Calculated for $C_{17}H_{25}N_3O_3$: C, 63.93; H, 7.89; N, 13.16; Found: C, 63.71; H, 8.01; N, 13.04.

EXAMPLE 11 b

5-[4-[4-(2-Hydroxyphenyl)-1-piperazinyl]butyl]-3-methyl-2-oxazolidinone.

Following the procedure of Example 5, a mixture of 5-(4-chlorobutyl)-3-methyl-2-oxazolidinone (5.39 g, 0.0282 mol), 1-(2-hydroxyphenyl)-piperazine dihydrobromide (9.6 g, 0.0282 mol), sodium bicarbonate (9.5 g, 0.113 mol) and potassium iodide (1.0 g) in n-butanol (100 mL) gave an oil which was triturated in light pet ether several times, crystallized from ethyl acetate/isopropyl ether, and dried under high vacuum at 50° C. to give 3.22 g (34% yield), mp 106°–110°.

Analysis: Calculated for $C_{18}H_{27}N_3O_3$: C, 64.84; H, 8.16; N, 12.60; Found: C, 64.79; H, 8.36; N, 12.54.

EXAMPLE 12

8-methyl-5-[4-[4-[2(2-propenyloxy)phenyl]-1-piperazinyl]butyl]-2-oxazolidinone hydrochloride hydrate (2:4:1).

To a stirring solution of 5-[4-[4(2-hydroxyphenyl)-1-piperazinyl]butyl-3-methyl-2-oxazolidinone (5.0 g, 0.0150 mol ) in absolute ethanol (150 mL) was added a solution of potassium hydroxide (0.93 g, 0.0165 mol) in absolute ethanol (100 mL). The mixture was stirred at room temperature for 30 minutes and allyl bromide (2.00 g, 0.0165 mol) was added. The mixture was stirred at room temperature for 3 hr and acidified with a 3N hydrochloric acid solution. The solvents were removed under reduced pressure and a saturated sodium bicarbonate solution and ethyl acetate were added. The layers were separated and the aqueous layer was extracted again with ethyl acetate. The combined organic layers were washed twice with a saturated sodium chloride solution, twice with a 5% potassium hydroxide solution, once more with a saturated sodium chloride solution, dried (sodium sulfate), filtered, and evaporated under reduced pressure to 3.7 g of a liquid, which was dissolved in absolute ethanol and acidified with ethanolic hydrogen chloride. The solid was collected by filtration, rinsed with diethyl ether and dried under high vacuum at 60° C., giving 3.15 g (46% yield), mp 197°–200° C.

Analysis: Calc. for $C_{21}H_{31}N_3O_3.2HCl.0.5H_2O$: C, 55.38; H, 7.52; N, 9.23; Found: C, 55.93; H, 7.62; N, 9.36.

EXAMPLE 13

5-[4-[4-(2-Methoxyphenyl)-1-piperazinyl]butyl]-3-phenyl-2-oxazolidinone hydrochloride hydrate (2:2:1).

Following the procedure of Example 5, a mixture of 5-(4-chlorobutyl)-3-phenyl-2-oxazolidinone (3.0 g, 0.01186 mol), 1(2methyoxyphenyl)-piperazine (2288g, 0.01186 mol), potassium carbonate (4.92 g, 0.0356 mol) and potassium iodide (1 g) in 1-butanol (75 ml) gave an oil (4.7 g, 87% yield), which was crystallized from isopropanol/isopropyl ether. Drying of the resulting solid under high vacuum gave 0.98 g, mp 153°–155° C.

Analysis: Calc. for $C_{24}H_{31}N_3O_3.HCl.0.5H_2O$: C, 63.36; H, 7.31; N, 9.24; Found: C, 63.60; H, 7.33; N, 9.12.

EXAMPLE 14

3-Phenyl-5-[4-[4-(2-pyridinyl)-1-piperazinyl]butyl]-2-oxazolidinone.

Following the procedure of Example 5, a mixture of 5-(4-chlorobutyl)-3-phenyl-2-oxazolidinone (3.0 g, 0.01186 mol), 1-(2-pyridinyl)piperazine (1.94 g, 0.01186 mol), potassium carbonate (4.92 g, 0.0356 mol), and potassium iodide (1.0 g) in n-butanol (75 mL) gave an oil, which crystallized upon standing (3.9 g, 86% yield). The solid was recrystallized from isopropanol/isopropyl ether and dried under high vacuum to give 1.80 g, mp 78°–81° C.

Analysis: Calculated for $C_{22}H_{28}N_4O_2$: C, 69.45; H, 7.42; N, 14.72; Found: C, 69.33; H, 7.51; N, 14.56.

EXAMPLE 15

3-Phenyl-5-[4-[4-(2-pyrimidinyl)-1-piperazinyl]butyl]-2-oxazolidinone.

Following the procedure of Example 5, a mixture of 5-(4-chlorobutyl)-3-phenyl-2-oxazolidinone (3.0 g, 0.01186 mol), 1-(2-pyrimidinyl)piperazine dihydrochloride (2.81 g, 0.01186 mol), potassium carbonate (9.85 g, 0.0713 mol), and potassium iodide (1.0 g) in n-butanol (75 mL) gave a solid (4.1 g, 91% yield). The solid was recrystallized from isopropanol/isopropyl ether and dried under high vacuum to give 2.58 g, mp 94°-96° C.

Analysis: Calculated for $C_{21}H_{27}N_5O_2$: C, 66.12; H, 7.13; N, 18.36; Found: C, 66.04; H, 7.17; N, 18.29.

EXAMPLE 16

3-Phenyl-5-[4-(4-phenyl-1-piperazinyl)butyl]-2-oxazolidinone.

Following the procedure of Example 5, a mixture of 5-(4-chlorobutyl)-3-phenyl-2-oxazolidinone (3.0 g, 0.01186 mol), 1-phenylpiperazine hydrochloride (2.35 g, 0.01186 mol), potassium carbonate (6.54 g, 0.0473 mol), and potassium iodide (1.0 g) in 1-butanol gave a liquid (4.1 g, 91% yield) which crystallized upon standing. Recrystallization from isopropanol/isopropyl/-ether and drying under high vacuum gave 1.44 g, mp 83°-85° C.

Analysis: Calculated for $C_{23}H_{29}N_3O_2$: C, 72.79; H, 7.70; N, 11.07; Found: C, 72.76; H, 7.90; N, 10.86.

EXAMPLE 17

5-[4-[4-(2-hydroxyphenyl)-1-piperazinyl]butyl]-3-phenyl-2-oxazolidinone.

Following the procedure of Example 5, a mixture of 5-(4-chlorobutyl)-3-phenyl-2-oxazolidinone (6.0 g, 0.0237 mol), 1-(2-hydroxyphenyl)piperazine dihydrobromide (8.06 g, 0.0237 mol), sodium bicarbonate (7.98 g, 0.095 mol), and potassium iodide (1.0 g) in n-butanol (200 mL) gave an oil (10.5 g) which crystallized on standing and was recrystallized from isopropanol/isopropyl ether. Drying under high vacuum gave 6.15 g (66% yield), mp 123°-129° C.

Analysis: Calculated for $C_{23}H_{29}N_3O_3$: C, 69.85; H, 7.39; N, 10.62; Found: C, 69.72; H, 7.52; N, 10.44.

EXAMPLE 18

5-[4-[4-(2-Ethoxyphenyl)-1-piperazinyl]butyl]-3-phenyl-2-oxazolidinone hydrochloride hydrate (2:4:1).

Following the procedure of Example 5, a mixture of 5-(4-chlorobutyl)-3-phenyl-2-oxazolidinone, (3.0 g, 0.01186 mol), 1-(2-ethoxyphenyl)piperazine hydrochloride (2.88 g, 0.01186 mol), potassium carbonate (6.57 g, 0.0475 mol), and potassium iodide (1.0 g) in n-butanol (100 mL) gave an oil (3.5 g, 79% yield). The oil was dissolved in ethanolic hydrogen chloride and allowed to stand. Diethyl ether was added to give a solid which was collected by filtration. After recrystallization the solid weighted 3.64 g, mp 215°-223° C.

Analysis: Calc. for $C_{26}H_{33}N_3O_3.2HCl.0.5H_2O$: C, 59.40; H, 7.18; N, 8.31; Found: C, 59.24; H, 7.22; N, 8.44.

EXAMPLE 19

3-Phenyl-5-[3-[4-(2-pyridinyl)-1-piperazinyl]propyl]-2-oxazolidinone.

Following the procedure of Example 5, a mixture of 5-(3-chloropropyl)-3-phenyl-2-oxazolidinone (4.5 g, 0.0188 mol), 1-(2-pyridinyl)piperazine (3.07 g, 0.0188 mol), potassium carbonate (7.81 g, 0.0565 mol), and potassium iodide (1.0 g) in n-butanol (200 mL) gave a solid which was recrystallized from isopropanol/isopropyl ether and dried under high vacuum to give 3.86 g (56% yield), mp 123°-125° C.

Analysis: Calculated for $C_{21}H_{26}N_4O_2$: C, 68.83; H, 7.15; N, 15.29; Found: C, 68.70; H, 7.16; N, 15.22.

EXAMPLE 20

3-Phenyl-5-[3-[4-(2-pyrimidinyl)-1-piperazinyl]propyl]2-oxazolidinone.

Following the procedure of Example 5, a mixture of 5-(3-chloropropyl)-3-phenyl-2-oxazolidinone (4.5 g, 0.0188 mol), 1-(2-pyrimidyl)piperazine dihydrochloride (4.47 g, 0.0188 mol), potassium carbonate (15.64 g, 0.113 mol), and potassium iodide (1.0 g) in n-butanol (200 mL) gave a solid which was recrystallized from isopropanol/isopropyl ether and dried under high vacuum to give 2.49 g (36% yield), mp 92°-98° C. and 118° C.

Analysis: Calculated for $C_{20}H_{25}N_5O_2$: C, 65.37; H, 6.86; N, 19.05; Found: C, 65.27; H, 6.85; N, 19.01.

EXAMPLE 21

5-[3-[4-(2-Ethoxyphenyl)-1-piperazinyl]propyl]-3-phenyl-2-oxazolidinone hydrochloride hydrate (2:4:1).

Following the procedure of Example 5, a mixture of 5-(3-chloropropyl)-3-phenyl-2-oxazolidinone (4.5 g, 0.0188 mol), 1-(2-ethoxyphenyl)piperazine hydrochloride (4.57 g, 0.0188 mol), potassium carbonate (10.42 g, 0.0754 mol), and potassium iodide (1.0 g) in n-butanol (200 mL) gave an oil. Acidification with ethanolic hydrogen chloride followed by addition of diethyl ether gave a solid, which was collected by filtration and dried under high vacuum to give 3.97 g (43% yield), mp 182°-187° C.

Analysis: Calculated for $C_{24}H_{31}N_3O_3.HCl.0.5H_2O$: C, 58.66; H, 6.97; N, 8.55; Found: C, 58.63; H, 7.10; N. 8.30.

EXAMPLE 22

3-Phenyl-5-[3-(4-phenyl)-1-piperazinyl]propyl]-2-oxazolidinone.

Following the procedure of Example 5, a mixture of 5-(3-chloropropyl)-3-phenyl-2-oxazolidinone (4.5 g, 0.0188 mol), 1-phenylpiperazine hydrochloride (3.74 g, 0.0188 mol), potassium carbonate (10.38 g, 0.0751 mol), and potassium iodide (1.0 g) in n-butanol (200 mL) gave a solid (6.2 g, 90% yield), Recrystallization from isopropanol/isopropyl ether and drying under high vacuum gave 2.60 g, mp 125°-127° C.

Analysis: Calculated for $C_{22}H_{27}N_3O_2$: C, 72.30; H, 74.5; N, 11.50; Found: C, 72.05; H, 7.48; N, 11.40.

EXAMPLE 23

5-[3-[4-(2-Methoxyphenyl)-1-piperazinyl]propyl]-3-phenyl-2-oxazolidinone hydrochloride hydrate (1:2).

Following the procedure of Example 5, a mixture of 5-(3-chloropropyl)-3-phenyl-2-oxazolidinone (4.5 g, 0.0188 mol), 1-(2-methoxyphenyl)-piperazine (3.62 g, 0.0188 mol), potassium carbonate (7.81 g, 0.0565 mol), and potassium iodide (1.0 g) in n-butanol (200 mL) gave an oil. The oil was acidified with warm ethanolic hydrogen chloride, filtered warm, and cooled to room temperature. Diethyl ether was added and the resulting solid was collected by filtration and dried under high vacuum at 50° C. to give 4.65 g (53% yield), mp 203°-211° C.

Analysis: Calculated for $C_{23}H_{29}N_3O_3.2HCl$: C, 58.98; H, 6.67; N, 8.97; Found: C, 59.02; H, 6.89; N, 8.93.

EXAMPLE 24

5-[3-[4-(2-Hydroxyphenyl)-1-piperazinyl]propyl]-3-phenyl-2-oxazolidinone hydrochloride (1:2).

Following the procedure of Example 5, a mixture of 5-(3-chloropropyl)-3-phenyl-2-oxazolidinone (9.0 g, 0.0376 mol), 1-(2-hydroxyphenyl)piperazine dihydrobromide (12.80 g, 0.0377 mol), sodium bicarbonate (12.66 g, 0.151 mol), and potassium iodide (1.0 g) in n-butanol (400 mL) gave an oil (9.3 g, 65% yield). The oil was dissolved in warm absolute ethanol and acidified with ethanolic hydrogen chloride. Ether was added and the solid was collected by filtration and dried under high vacuum at 60° C. to give 8.28 g, mp 250° C.

Analysis: Calculated for $C_{22}H_{27}N_3O_2.2HCl$: C, 58.15; H, 6.43; N, 9.25; Found: C, 58.00; H, 6.51; N, 9.20.

EXAMPLE 25

3-Phenyl-5-[4-[4-[2-[2-propenyloxyl)phenyl]-1-piperazinyl]butyl]-2-oxazolidinone hydrochloride (1:2).

A mixture of 5-[4-[4-(2-hydroxyphenyl)-1-piperazinyl]butyl]-3-phenyl-2-oxazolidinone (4.0 g, 0.0101 mol) and potassium hydroxide (0.62 g, 0.011 mol) in absolute ethanol (250 mL) was stirred at room temperature for two hours and allyl bromide (1.34 g, 0.0111 mol) was added. The mixture was stirred at room temperature for 4 days and then acidified with a 3N hydrochloric acid solution. The solvents were removed under reduced pressure and then the residue was dissolved in a saturated sodium bicarbonate solution. The product was extracted twice into ethyl acetate, washed once with water, twice with a 5% potassium hydroxide solution, once again with water and once with a saturated sodium chloride solution, dried (sodium sulfate), filtered and evaporated under reduced pressure to an oil (4.3 g, 98% yield). The oil was dissolved in warm absolute ethanol and acidified with ethanolic hydrogen chloride. The resulting solid was collected by filtration, rinsed with ether and dried under high vacuum at 50° C. to give 3.5 g, mp 198°-202° C.

Analysis: Calculated for $C_{26}H_{33}N_3O_3.2HCl$: C, 61.41; H, 6.94; N, 8.26; Found: C, 60.98; H, 7.12; N, 8.18.

EXAMPLE 26

3-Phenyl-5-[3-[4-[2-(2-propenyloxy)phenyl]-1-piperazinyl]propyl]-2-oxazolidinone hydrochloride hydrate (2:2:3).

A mixture of 5-[3-[4-(2-hydroxyphenyl)-1-piperazinyl]propyl]-3-phenyl-2-oxazolidinone dihydrochloride (4.0 g, 0.0101 mol) and potassium hydroxide (0.62 g, 0.0111 mol) in absolute ethanol (250 mL) was stirred at room temperature for two hours and allyl bromide (1.34 g, 0.0111 mol) was added. The mixture was stirred at room temperature for 4 days and then acidified with a 3N hydrochloric acid solution. The solvents were removed under reduced pressure and a saturated sodium bicarbonate solution was added to the residue. The product was extracted twice into ethyl acetate and the combined extracts were washed once with water, twice with a 5% potassium hydroxide solution, once again with water and once with a saturated sodium chloride solution, dried (sodium sulfate), filtered and evaporated under reduced pressure to an oil (4.3 g, 98% yield). The oil was dissolved in warm absolute ethanol and acidified with ethanolic hydrogen chloride. The resulting solid was collected by filtration, rinsed with ether and dried under high vacuum at 50° C. to give 3.5 g, mp 198°-202° C.

Analysis: Calculated for $C_{25}H_{31}N_3O_3.HCl.1.5H_2O$: C, 61.91; H, 7.27; N, 8.66; Found: C, 62.19; H, 6.91; N, 8.84.

EXAMPLE 27

5-[4-[4-(2-methoxyphenyl)-1-piperazinyl]butyl]-3-(1-methylethyl)-2-oxazolidinone hydrochloride (1:2).

Following the procedure of Example 5, a mixture of 5-(4-chlorobutyl)-3-(1-methylethyl)-2-oxazolidinone (5.2 g, 0.0237 mol), 1-(2-methoxyphenyl)piperazine (4.56 g, 0.0237 mol), potassium carbonate (9.84 g, 0.0712 mol) and potassium iodide (1.0 g) in n-butanol (200 mL) gave an oil. The oil was dissolved in absolute ethanol and acidified with ethanolic hydrogen chloride. Addition of ether gave a solid which was collected by filtration and dried under high vacuum at 70° C. to give 7.36 g (69% yield), mp 206°-213° C.

Analysis: Calculated for $C_{21}H_{33}N_3O_3.2HCl$: C, 56.25; H, 7.87; N, 9.37; Found: C, 56.18; H, 8.13; N, 9.31.

EXAMPLE 28

5-[4-[4-(2-Ethoxyphenyl)-1-piperazinyl butyl]-3-(1-methylethyl)-2-oxazolidinone hydrochloride (1:2).

Following the procedure of Example 5, a mixture of 5-(4-chlorobutyl)-3-(1-methylethyl)-2-oxazolidinone (5.2 g, 0.0137 mol), 1-(2-ethoxyphenyl)-piperazine hydrochloride (5.76 g, 0.0237 mol) and potassium iodide (1.0 g) in N-butanol (200 mL) gave an oil. The oil was dissolved in absolute ethanol and acidified with ethanolic hydrogen chloride. Addition of ether and filtration gave a solid which was dried under high vacuum at 70° C. to give 6.62 g (60% yield), mp 199°-205° C.

Analysis: Calculated for $C_{22}H_{35}N_3O_3.2HCl$: C, 57.14; H, 8.06; N, 9.09; Found: C, 57.25; H, 8.42; N, 9.07.

EXAMPLE 29

5-[4-[4-(2-Hydroxyphenyl)-1-piperazinyl]butyl]-3-(1-methylethyl)-2-oxazolidinone hydrochloride (1:2).

Following the procedure of Example 5, a mixture of 5-(4-chlorobutyl)-3-(1-methylethyl)-2-oxazolidinone (10.4 g, 0.0474 mol), 1-(2-hydroxyphenyl)piperazine dihydrobromide (16.12 g, 0.0474 mol), sodium bicarbonate (15.96 g, 0.190 mol) and potassium iodide (1.0) in n-butanol (350 mL) gave an oil. The oil was dissolved in absolute ethanol and acidified with ethanolic hydrogen chloride. Addition of ether and filtration gave a solid which was dried under high vacuum at 70° C. to give 9.47 g (46% yield), mp 203°-207° C.

Analysis: Calculated for $C_{20}H_{31}N_3O_3.2HCl$: C, 55.30; H, 7.66; N, 9.67; Found: C, 54.97; H, 7.97; N, 9.49.

TABLE I

Formula I Examples

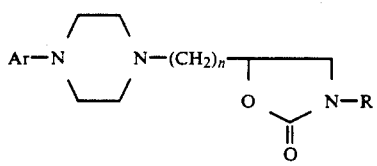

| Examples | Ar | n | R |
|---|---|---|---|
| 1 | $C_6H_5$ | 4 | $-CH_3$ |
| 2 | 2-pyridinyl | 4 | $-CH_3$ |
| 3 | 2-$CH_3OC_6H_4-$ | 4 | $-CH_3$ |
| 4 | 2-pyrimidinyl | 4 | $-CH_3$ |
| 5 | 2-$CH_3OC_6H_4-$ | 3 | $-CH_3$ |
| 6 | 2-pyridinyl | 3 | $-CH_3$ |
| 7 | 2-pyrimidinyl | 3 | $-CH_3$ |
| 8 | 2-$C_2H_5OC_6H_4-$ | 3 | $-CH_3$ |
| 9 | 2-$C_2H_5OC_6H_4-$ | 4 | $-CH_3$ |
| 10 | 2-$HOC_6H_4-$ | 3 | $-CH_3$ |
| 11 | 2-$HOC_6H_4-$ | 4 | $-CH_3$ |
| 12 | 2-$(CH_2=CHCH_2O)C_6H_4-$ | 4 | $-CH_3$ |
| 13 | 2-$CH_3OC_6H_4-$ | 4 | $-C_6H_5$ |
| 14 | 2-pyridinyl | 4 | $-C_6H_5$ |
| 15 | 2-pyrimidinyl | 4 | $-C_6H_5$ |
| 16 | $C_6H_5$ | 4 | $-C_6H_5$ |
| 17 | 2-$HOC_6H_4-$ | 4 | $-C_6H_5$ |
| 18 | 2-$C_2H_5OC_6H_4-$ | 4 | $-C_6H_5$ |
| 19 | 2-pyridinyl | 3 | $-C_6H_5$ |
| 20 | 2-pyrimidinyl | 3 | $-C_6H_5$ |
| 21 | 2-$C_2H_5OC_6H_4-$ | 3 | $-C_6H_5$ |
| 22 | $C_6H_5-$ | 3 | $-C_6H_5$ |
| 23 | 2-$CH_3OC_6H_4-$ | 3 | $-C_6H_5$ |
| 24 | 2-$HOC_6H_4-$ | 3 | $-C_6H_5$ |
| 25 | 2-$(CH_2=CHCH_2O)C_6H_4-$ | 4 | $-C_6H_5$ |
| 26 | 2-$(CH_2=CHCH_2O)C_6H_4-$ | 3 | $-C_6H_5$ |
| 27 | 2-$CH_3OC_6H_4-$ | 4 | $-CH(CH_3)_2$ |
| 28 | 2-$C_2H_5OC_6H_4-$ | 4 | $-CH(CH_3)_2$ |
| 29 | 2-$HOC_6H_4-$ | 4 | $-CH(CH_3)_2$ |

PHARMACOLOGY

Anxiolytic test data obtained (competitive binding to $5HT_{1A}$ receptors or expiratory light/dark behavior) for the invention compounds and a reference compound are shown in Table II.

TABLE II

Pharmacology Data

| Example | $5HT_{1A}$[1] | Light/Dark[2] | Example | $5HT_{1A}$ | Light/Dark[2] |
|---|---|---|---|---|---|
| 1 | 59 | 56 (10) | 16 | 8.2 | — |
| 2 | 61 | 53 (3.16) | 17 | 15 | — |
| 3 | 15 | 53 (3.16) | 18 | 2.0 | — |
| 4 | 190 | — | 19 | 57 | — |
| 5 | 29 | — | 20 | 170 | — |
| 6 | 110 | — | 21 | 18 | — |
| 7 | 510 | — | 22 | 50 | — |
| 8 | 22 | — | 23 | 11 | — |
| 9 | 16 | — | 24 | — | — |
| 10 | 110 | — | 25 | — | — |
| 11 | 40 | — | 26 | — | — |
| 12 | 20 | 66 (1) | 27 | — | — |
| 13 | 2.2 | — | 28 | — | — |
| 14 | 7.7 | — | 29 | — | — |
| 15 | 29 | — | Buspirone 13.2 (avg) | 51 (5.62) IP 54 (5.62) PO | |

[1]$IC_{50}$ (nMol)
[2]% time spent in lit area (dose, mg/kg IP), minimum effective dose

PHARMACEUTICAL COMPOSITION

The pharmaceutical compositions used in the methods of this invention for administration to living animals are comprised of, as active ingredients, at least one of the compounds of Formula I according to this invention, in association with a pharmaceutical carrier or excipient. The compounds are thus presented in a therapeutic composition for oral, parenteral, or rectal administration. Thus for example, compositions for oral administration can take the form of elixirs, capsules, tablets or coated tablets containing carriers conveniently used in the pharmaceutical art. Suitable tableting excipients include lactose, potato and maize starches, talc, gelatin, stearic and silicic acids, magnesium stearate and polyvinyl pyrrolidones.

For parenteral administration, the carrier or excipient can be comprised of a sterile parenterally acceptable liquid, e.g., water or arachis oil contained in ampoules.

In compositions for rectal administration, the carrier can be comprised of a suppository base, e.g., cocoa butter or a glyceride.

Advantageously, the compositions are formulated as dosage units, each unit being adapted to supply a fixed dose of active ingredients. Tablets, coated tablets, capsules, ampoules and suppositories are examples of preferred dosage forms according to the invention. It is only necessary that the active ingredient constitute an effective amount; i.e., such that a suitable dosage will be consistent with the dosage form employed in single or multiple unit doses. The exact individual dosages, as well as daily dosages, will, of course, be determined according to standard medical principles under the direction of a physician or veterinarian.

Generally, the pharmacology tests suggest a contemplated effective oral dose for humans will be in the range of 2–200 mg daily to be taken in divided doses of from 0.5 to 50 mg 3 to 4 times daily.

What is claimed is:

1. A method of treating anxiety by internally administering to a warm blooded animal in need thereof an anxiolytic amount of a compound of the formula:

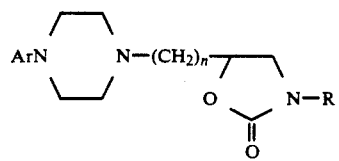

wherein n is 3 or 4, R is $C_1$–$C_4$ alkyl or phenyl, and Ar is

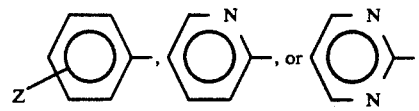

where Z is H, $C_1$–$C_4$ alkoxy, $C_2$–$C_4$ alkenyloxy or hydroxy, the stereoisomers, or a pharmaceutically acceptable salt thereof.

2. The method according to claim 1 where the compound used is 3-methyl-5-[4-[4-(2-pyridinyl)-1-piperazinyl]butyl]-2-oxazolidinone, a stereoisomer, or a pharmaceutically acceptable salt thereof.

3. The method according to claim 1 where the compound used is 5-[4-[4-(2-methoxyphenyl)-1-piperazinyl]butyl]-3-methyl-2-oxazolidinone, a stereoisomer, or a pharmaceutically acceptable salt thereof.

4. The method according to claim 1 where the compound used is 5-[3-[4-(2-methoxyphenyl)-1-piperazinyl]- propyl]-3-methyl-2-oxazolidinone, a stereoisomer, or a pharmaceutically acceptable salt thereof.

5. The method according to claim 1 wherein the compound used is 5-[3-[4-(2-ethoxyphenyl)-1-piperazinyl]propyl]-3-methyl-2-oxazolidinone, a stereoisomer, or a pharmaceutically acceptable salt thereof.

6. The method according to claim 1 where the compound used is 5-[4-[4-(2-ethoxyphenyl)-1-piperazinyl]butyl]-3-methyl-2-oxazolidinone, a stereoisomer, or a pharmaceutically acceptable salt thereof.

7. The method according to claim 1 where the compound used is 5-[4-[4-(2-hydroxyphenyl)-1-piperazinyl]butyl]-3-methyl-2-oxazolidinone, a stereoisomer, or a pharmaceutically acceptable salt thereof.

8. The method according to claim 1 where the compound used is 3-methyl-5-[4-[4-(2-propenyloxyphenyl)-1-piperazinyl]butyl]-2-oxazolidinone, a stereoisomer, or a pharmaceutically acceptable salt thereof.

9. The method according to claim 1 where the compound used is 5-[4-[4-(2-methoxyphenyl)-1-piperazinyl]butyl]-3-phenyl-2-oxazolidinone, a stereoisomer, or a pharmaceutically acceptable salt thereof.

10. The method according to claim 1 where the compound used is 3-phenyl-5-[4-[4-(2-pyridinyl)-1-piperazinyl]butyl]-2-oxazolidinone, a stereoisomer, or a pharmaceutically acceptable salt thereof.

11. The method according to claim 1 where the compound used is 3-phenyl-5-[4-[4-(2-pyrimidinyl)-1-piperazinyl]butyl]-2-oxazolidinone, a stereoisomer, or a pharmaceutically acceptable salt thereof.

12. The method according to claim 1 where the compound used is 3-phenyl-5-[4-(4-phenyl-1-piperazinyl)-butyl]-2-oxazolidinone, a stereoisomer, or a pharmaceutically acceptable salt thereof.

13. The method according to claim 1 where the compound used is 5-[4-[4-(2-hydroxyphenyl)-1-piperazinyl]butyl]-3-phenyl-2-oxazolidinone, a stereoisomer, or a pharmaceutically acceptable salt thereof.

14. The method according to claim 1 where the compound used is 5-[4-[4-(2-ethoxyphenyl)-1-piperazinyl]butyl]-3-phenyl-2-oxazolidinone, a stereoisomer, or a pharmaceutically acceptable salt thereof.

15. The method according to claim 1 where the compound used is 3-phenyl-5-[3-[4-(2-pyridinyl)-1-piperazinyl]propyl]-2-oxazolidinone, a stereoisomer, or a pharmaceutically acceptable salt thereof.

16. The method according to claim 1 where the compound used is 5-[3-[4-(2-ethoxyphenyl)-1-piperazinyl]propyl]-3-phenyl-2-oxazolidinone, a stereoisomer, or a pharmaceutically acceptable salt thereof.

17. The method according to claim 1 where the compound used is 3-phenyl-5-[3-(4-phenyl)-1-piperazinyl]propyl]-2-oxazolidinone, a stereoisomer, or a pharmaceutically acceptable salt thereof.

18. The method according to claim 1 where the compound used is 5-[3-[4-(2-methoxyphenyl)-1-piperazinyl]propyl]3-phenyl-2-oxazolidinone, a stereoisomer, or a pharmaceutically acceptable salt thereof.

* * * * *